United States Patent
Bae et al.

(10) Patent No.: US 9,916,844 B2
(45) Date of Patent: *Mar. 13, 2018

(54) METHOD FOR DETERMINING ALCOHOL CONSUMPTION, AND RECORDING MEDIUM AND TERMINAL FOR CARRYING OUT SAME

(71) Applicant: Foundation of Soongsil University-Industry Cooperation, Seoul (KR)

(72) Inventors: Myung Jin Bae, Seoul (KR); Sang Gil Lee, Busan (KR); Geum Ran Baek, Seoul (KR)

(73) Assignee: FOUNDATION OF SOONGSIL UNIVERSITY-INDUSTRY COOPERATION, Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 15/115,118

(22) PCT Filed: Jan. 28, 2014

(86) PCT No.: PCT/KR2014/000780
§ 371 (c)(1),
(2) Date: Jul. 28, 2016

(87) PCT Pub. No.: WO2015/115677
PCT Pub. Date: Aug. 6, 2015

(65) Prior Publication Data
US 2016/0379669 A1    Dec. 29, 2016

(30) Foreign Application Priority Data
Jan. 28, 2014   (KR) .................. 10-2014-0010173

(51) Int. Cl.
*G10L 25/66* (2013.01)
*G10L 17/26* (2013.01)
(Continued)

(52) U.S. Cl.
CPC ............ *G10L 25/66* (2013.01); *A61B 5/4803* (2013.01); *A61B 5/4845* (2013.01); *G10L 15/02* (2013.01);
(Continued)

(58) Field of Classification Search
None
See application file for complete search history.

(56) References Cited

U.S. PATENT DOCUMENTS 5,776,055 A    7/1998   Hayre
5,913,188 A *  6/1999   Tzirkel-Hancock .... G10L 15/02
                                                      704/221
(Continued)

FOREIGN PATENT DOCUMENTS

EP    1850328 A1    10/2007
JP    2003-36087 A   2/2003
(Continued)

OTHER PUBLICATIONS

Chan-Joong Jung et al. "Speech Sobriety Test Based on Formant Energy Distribution" International Journal of Multimedia and Ubiquitous Engineering vol. 8 No. 6 (2013), pp. 209-216.
(Continued)

*Primary Examiner* — Pierre-Louis Desir
*Assistant Examiner* — Jonathan Kim
(74) *Attorney, Agent, or Firm* — Sang Ho Lee; Novick, Kim & Lee, PLLC

(57) ABSTRACT

Disclosed are a method for determining whether a person is drunk after consuming alcohol on the basis of a difference
(Continued)

among a plurality of formant energy energies, which are generated by applying linear predictive coding according to a plurality of linear prediction orders, and a recording medium and a terminal for carrying out the method. The alcohol consumption determining terminal comprises: a voice input unit for receiving voice signals and converting same into voice frames and outputting the voice frames; a voiced/unvoiced sound analysis unit for extracting voice frames corresponding to a voiced sound from among the voice frames; an LPC processing unit for calculating a plurality of formant energy energies by applying linear predictive cording according to the plurality of linear prediction orders to the voice frames corresponding to the voiced sound; and an alcohol consumption determining unit for determining whether a person is drunk after consuming alcohol on the basis of a difference among the plurality of formant energy energies which have been calculated by the LPC processing unit, thereby determining whether a person is drunk after consuming alcohol depending on a change in the formant energy energies generated by applying linear predictive coding according to the plurality of linear prediction orders to voice signals.

18 Claims, 6 Drawing Sheets

(51) Int. Cl.
G10L 25/15 (2013.01)
A61B 5/00 (2006.01)
G10L 15/02 (2006.01)
G10L 15/16 (2006.01)
G10L 19/12 (2013.01)
G10L 25/84 (2013.01)

(52) U.S. Cl.
CPC .............. *G10L 15/16* (2013.01); *G10L 17/26* (2013.01); *G10L 19/12* (2013.01); *G10L 25/15* (2013.01); *G10L 25/84* (2013.01)

(56) References Cited

U.S. PATENT DOCUMENTS

| | | | | |
|---|---|---|---|---|
| 5,983,189 | A * | 11/1999 | Lee | G08B 21/06 704/273 |
| 6,006,188 | A * | 12/1999 | Bogdashevsky | G10L 17/26 704/270 |
| 6,205,420 | B1 * | 3/2001 | Takagi | G10L 21/04 704/200 |
| 6,275,806 | B1 * | 8/2001 | Pertrushin | G10L 17/26 704/270 |
| 6,446,038 | B1 * | 9/2002 | Bayya | G10L 25/69 704/231 |
| 6,748,301 | B1 | 6/2004 | Ryu | |
| 7,925,508 | B1 | 4/2011 | Michaelis | |
| 7,962,342 | B1 | 6/2011 | Coughlan et al. | |
| 8,478,596 | B2 | 7/2013 | Schultz | |
| 8,938,390 | B2 * | 1/2015 | Xu | A61B 5/7264 704/231 |
| 9,058,816 | B2 * | 6/2015 | Lech | G10L 17/26 |
| 9,659,571 | B2 | 5/2017 | Van Der Schaar | |
| 9,672,809 | B2 | 6/2017 | Togawa et al. | |
| 2002/0010587 | A1 * | 1/2002 | Pertrushin | G10L 17/26 704/275 |
| 2002/0194002 | A1 * | 12/2002 | Petrushin | G10L 17/26 704/270 |
| 2003/0069728 | A1 * | 4/2003 | Tato | G10L 17/26 704/231 |
| 2004/0167774 | A1 * | 8/2004 | Shrivastav | G10L 17/26 704/207 |
| 2005/0075864 | A1 * | 4/2005 | Kim | G10L 25/48 704/206 |
| 2005/0102135 | A1 * | 5/2005 | Goronzy | G10L 15/00 704/213 |
| 2007/0071206 | A1 * | 3/2007 | Gainsboro | H04M 3/2281 379/168 |
| 2007/0124135 | A1 | 5/2007 | Schultz | |
| 2007/0192088 | A1 * | 8/2007 | Oh | G10L 15/02 704/209 |
| 2007/0213981 | A1 * | 9/2007 | Meyerhoff | G10L 17/26 704/243 |
| 2007/0288236 | A1 | 12/2007 | Kim | |
| 2009/0265170 | A1 | 10/2009 | Irie et al. | |
| 2010/0010689 | A1 | 1/2010 | Yasushi et al. | |
| 2011/0035213 | A1 * | 2/2011 | Malenovsky | G10L 25/78 704/208 |
| 2011/0282666 | A1 * | 11/2011 | Washio | G10L 17/26 704/246 |
| 2012/0089396 | A1 * | 4/2012 | Patel | G10L 25/00 704/249 |
| 2012/0116186 | A1 * | 5/2012 | Shrivastav | A61B 5/0507 600/301 |
| 2012/0262296 | A1 * | 10/2012 | Bezar | G10L 17/26 340/573.1 |
| 2013/0006630 | A1 * | 1/2013 | Hayakawa | G10L 17/26 704/239 |
| 2013/0253933 | A1 | 9/2013 | Maruta | |
| 2014/0122063 | A1 * | 5/2014 | Gomez Vilda | G10L 19/02 704/200.1 |
| 2014/0188006 | A1 * | 7/2014 | Alshaer | A61B 5/7282 600/586 |
| 2014/0379348 | A1 * | 12/2014 | Sung | G10L 25/75 704/254 |
| 2015/0127343 | A1 | 5/2015 | Mullor et al. | |
| 2015/0257681 | A1 | 9/2015 | Shuster et al. | |
| 2015/0310878 | A1 * | 10/2015 | Bronakowski | G10L 25/63 704/246 |
| 2015/0351663 | A1 * | 12/2015 | Zigel | A61B 5/4803 600/586 |
| 2016/0155456 | A1 | 6/2016 | Wang | |
| 2016/0379669 | A1 | 12/2016 | Bae et al. | |
| 2017/0004848 | A1 | 1/2017 | Bae et al. | |

FOREIGN PATENT DOCUMENTS

| | | |
|---|---|---|
| JP | 2010-015027 A | 1/2010 |
| JP | 5017534 B2 | 9/2012 |
| KR | 10-1997-0038004 A | 7/1997 |
| KR | 10-0201256 B1 | 6/1999 |
| KR | 10-1999-0058415 A | 7/1999 |
| KR | 10-0206205 B1 | 7/1999 |
| KR | 10-2004-0033783 A | 4/2004 |
| KR | 10-0497837 B1 | 6/2005 |
| KR | 10-0664271 B1 | 1/2007 |
| KR | 10-2009-0083070 A | 8/2009 |
| KR | 10-2012-0074314 A | 7/2012 |
| WO | 2012/014301 A1 | 2/2012 |

OTHER PUBLICATIONS

Geumran Baek et al. "A Study on Voice Sobriety Test Algorithm in a Time-Frequency Domain" International Journal of Multimedia and Ubiquitous Engineering vol. 8 No. 5 (2013), pp. 395-402.

Geumran Baek et al. "A Study on Judgment of Intoxication State Using Speech," Information and Telecommunication Department, Soongsil University, pp. 277-282.

Seong-Geon Bae et al. "A Study on Personalized Frequency Bandwidth of Speech Signal using Formant to LPC," The Journal of Korean Institute of Communications and Information Sciences (winter), 2013, pp. 669-670.

Seong-Geon Bae et al. "A Study on Drinking Judgement Method of Speech Signal Using the Fomant Deviation in the Linear Prediction Coefficient," he Journal of Korean Institute of Communications and Information Sciences (winter), 2013, pp. 667-668.

Bocklet, Tobias, Korbinian Riedhammer, and Elmar Noth. "Drink and Speak: On the automatic classification of alcohol intoxication

(56) References Cited

OTHER PUBLICATIONS by acoustic, prosodic and text-based features." Twelfth Annual Conference of the International Speech Communication Association. 2011.
Chan Joong Jung et al. "A Study on Drunken Decision using Spectral Envelope Changes" Korea Institute of Communications and Information Sciences, Winter Conference, vol. 2013 No. 1 (2013), pp. 674-675.
Lee, Won Hui et al. "Valid-frame Distance Deviation of Drunk and non-Drunk Speech" The Journal of Korea Information and Communications Society (winter) 2014, pp. 876-877, Jan. 2014.
Jung, Chan Joong et al. "A Study on Detecting Decision Parameter about Drinking in Time Domain," The Journal of Korea Information and Communications Society (winter) 2014, pp. 784-785, Jan. 2013.
Lee, Won-Hee et al.."A Study on Drinking Judgement using Differential Signal in Speech Signal", The Journal of Korea Information and Communications Society (winter) 2014, pp. 878-879, Jan. 2014.
Seong Geon Bae, Dissertation for Ph.D, "A study on Improving Voice Surveillance System Against Drunk Sailing". Information and Communication Engineering Dept., Soongsil University, Republic of Korea. Dec. 2013. (English Abstract at pp. x-xii).
Tae-Hun Kim et al. "Drinking Speech System", Department of Information Communication, Sang Myung University, pp. 257-262.
See-Woo Lee, "A Study on Formant Variation with Drinking and Nondrinking Condition," Department of Information & Telecommunication Engineering, Sangmyung University, vol. 10, No. 4, pp. 805-810, 2009.
Sato (Sato, Nobuo, and Yasunari Obuchi. "Emotion recognition using mel-frequency cepstral coefficients." Information and Media Technologies 2.3 (2007): 835-848.).
Baumeister, Barbara, Christian Heinrich, and Florian Schiel. "The influence of alcoholic intoxication on the fundamental frequency of female and male speakers." The Journal of the Acoustical Society of America 132.1 (2012): 442-451.
Schuller, Bjorn W., et al. "The INTERSPEECH 2011 Speaker State Challenge." INTERSPEECH. 2011.
Hollien, Harry, et al. "Effects of ethanol intoxication on speech suprasegmentals." The Journal of the Acoustical Society of America 110.6 (2001): 3198-3206.
Kim (Kim, Jonathan, Hrishikesh Rao, and Mark Clements. "Investigating the use of formant based features for detection of affective dimensions in speech." Affective computing and intelligent interaction (2011): 369-377.).
Broad (Broad, David J., and Frantz Clermont. "Formant estimation by linear transformation of the LPC cepstrum." The Journal of the Acoustical Society of America 86.5 (1989)).

\* cited by examiner

METHOD FOR DETERMINING ALCOHOL CONSUMPTION, AND RECORDING MEDIUM AND TERMINAL FOR CARRYING OUT SAME

TECHNICAL FIELD

The present invention relates to a method of determining whether a person is drunk after consuming alcohol using a voice analysis, and a recording medium and terminal for carrying out the same.

BACKGROUND ART

Although there may be differences among individuals, a drunk driving accident is likely to happen when a driver is half-drunk or drunk. As methods of measuring drunkenness, there are a method of measuring the concentration of alcohol in exhaled air during respiration using a breathalyzer equipped with an alcohol sensor and a method of measuring the concentration of alcohol in the blood flow using laser. Generally, the former method is usually used for cracking down on drunk driving. In this case, when any driver refuses a drunkenness test, Widmark Equation may be used to estimate a blood alcohol concentration by collecting the blood of the driver with his or her consent.

A technology for determining whether a driver has consumed alcohol and controlling a starting device of a vehicle in order to prevent drunk driving is commercialized. Some vehicles to which the technology is applied are already commercially available. Such a technology works by enabling or disabling a vehicle to be started by attaching a detection device equipped with an alcohol sensor to a starting device of the vehicle and is a field in which much research is being conducted by domestic and foreign automotive manufacturers. These methods use an alcohol sensor and thus may relatively accurately measure a concentration of alcohol. However, in an environment with high humidity and dust, such as an automotive interior environment, the alcohol sensor has a low accuracy and is not semi-permanently usable due to frequent failures. Furthermore, the sensor has a short lifetime. Accordingly, when the sensor is combined to an electronic device, there is an inconvenience of having to repair the electronic device in order to replace the sensor.

PRIOR ART DOCUMENTS

Patent Documents

Korean Publication No. 10-2012-0074314
Korean Patent No. 10-0664271

DISCLOSURE

Technical Problem

An aspect of the present invention is directed to a method for determining whether a person is drunk after consuming alcohol on the basis of a difference among a plurality of formant energies that are generated by applying linear predictive coding according to a plurality of linear prediction orders and a recording medium and a terminal for carrying out the method.

Technical Solution

According to an aspect of the present invention, an alcohol consumption determination method includes: receiving a voice signal and converting the received voice signal into a plurality of voice frames; extracting a voice frame corresponding to a voiced sound from among the plurality of voice frames; calculating a plurality of formant energies by applying linear predictive coding according to a plurality of linear prediction orders to the voice frame corresponding to a voiced sound; and calculating differences among the plurality of formant energies and determining whether alcohol has been consumed according to the differences.

The calculating of differences among the plurality of formant energies may include finding two formant energies by applying two linear prediction orders to the voice frame determined as the voiced sound and calculating a difference between the two formant energies as a distance.

The calculating of differences among the plurality of formant energies and the determining of whether alcohol has been consumed according to the differences may include calculating average energy of the differences among the plurality of formant energies for the voice frame determined as the voiced sound and finding an average energy ratio between a previous voice frame and a current voice frame to determine whether alcohol has been consumed.

The finding of an average energy ratio between a previous voice frame and a current voice frame to determine whether alcohol has been consumed may include calculating the average energy ratio between the previous voice frame and the current voice frame for each of all voice frames determined as voiced sounds, count the number of voice frames each having average energy greater than a predetermined threshold, and determining whether alcohol has been consumed according to the counted number.

The determining of whether alcohol has been consumed according to the counted number may include calculating a ratio between the counted number and the total number of voice frames determined as the voiced sounds, determining that alcohol has been consumed when the calculated ratio is less than a predetermined value, and determining that alcohol has not been consumed when the calculated ratio is greater than the predetermined value.

The calculating of a plurality of formant energies by applying linear predictive coding according to a plurality of linear prediction orders to the voice frame corresponding to the voiced sound may include applying a low order linear prediction order and a high order linear prediction order to the voice frame corresponding to the voiced sound to calculate formant energies according to the linear prediction orders.

The alcohol consumption determination method may further include filtering out harmonics of a certain frequency or higher by applying a low pass filter to the voice frame corresponding to the voiced sound.

According to an embodiment of the present invention, a computer-readable recording medium has a program recorded thereon for performing the above-described alcohol consumption determination method.

According to an embodiment of the present invention, an alcohol consumption determination terminal includes a voice input unit configured to receive a voice signal and convert the received voice signal into voice frames; a voiced/unvoiced sound analysis unit configured to extract a voice frame corresponding to a voiced sound from among the voice frames; an linear predictive coding (LPC) processing unit configured to calculate a plurality of formant energies by applying LPC according to a plurality of linear prediction orders to the voice frame corresponding to the voiced sound; and an alcohol consumption determination unit configured to determine whether alcohol has been consumed according to differences among the plurality of formant energies calculated by the LPC processing unit.

The alcohol consumption determination terminal may further include a low pass filter (LPF) application unit configured to filter out signals of a certain frequency or higher for the voice frame analyzed as the voiced sound by the voiced/unvoiced sound analysis unit.

The LPC processing unit may extract two formant energies by applying the LPC according to two linear prediction orders to the voice frame analyzed as the voiced sound.

The alcohol consumption determination unit may include a difference calculation unit configured to calculate the differences among the plurality of formant energies that are generated by applying the LPC according to the plurality of linear prediction orders.

The alcohol consumption determination unit may further include an average energy calculation unit configured to calculate average energy of the differences among the plurality of formant energies calculated by the difference calculation unit.

The alcohol consumption determination unit may further include a counting unit configured to calculate a ratio between average energy of formant energy differences of a previous voice frame and average energy of formant energy differences of a current voice frame and count the number of voice frames each having a ratio greater than a predetermined threshold.

The alcohol consumption determination unit may further include a determination unit configured to calculate a ratio of the number counted by the counting unit to the total number of voice frames analyzed as the voiced sounds and determine that alcohol has been consumed when the ratio is less than a predetermined value.

Advantageous Effects

As described above, according to an aspect of the present invention, whether alcohol has been consumed may be determined according to a variation of formant energy that is generated by applying linear predictive coding to a voice signal according to a plurality of linear prediction orders.

MODES FOR CARRYING OUT THE INVENTION

Hereinafter, exemplary embodiments of the present invention will be described in detail with reference to the accompanying drawings. In adding reference numbers for elements in each figure, it should be noted that like reference numbers already used to denote like elements in other figures are used for elements wherever possible.

Figure 1A:
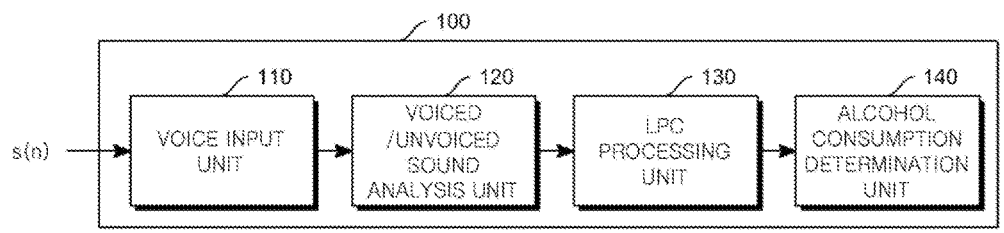
FIGS. 1A and 1B are control block diagrams of an alcohol consumption determination terminal according to an embodiment of the present invention.
Figure 1B:
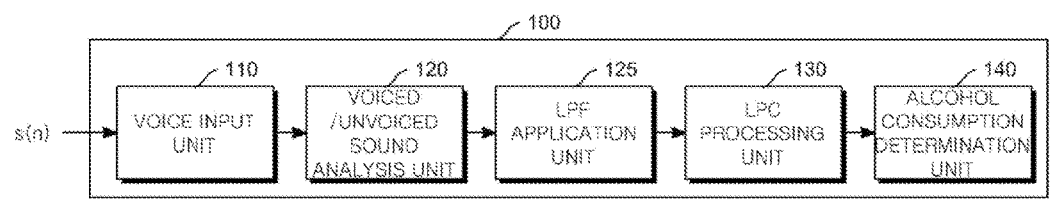

FIGS. 1A and 1B are control block diagrams of an alcohol consumption determination terminal according to an embodiment of the present invention.

Referring to FIG. 1A, an alcohol determination terminal 100 may include a voice input unit 110, a voiced/unvoiced sound analysis unit 120, a linear predictive coding (LPC) processing unit 130, and an alcohol consumption determination unit 140.

The voice input unit 110 may receive a person's voice, convert the received voice into voice data, convert the voice data into voice frame data in units of frames, and output the voice frame data. The voice input unit 110 may convert voice signals in a frequency domain using a transform method such as Fast Fourier Transform (FFT).

The voiced/unvoiced sound analysis unit 120 may receive a voice frame, extract predetermined features from the voice frame, and analyze whether the voice frame is associated with a voiced sound, an unvoiced sound, or noise according to the extracted features.

The voiced/unvoiced sound analysis unit 120 may determine whether the voice frame corresponds to a voiced sound, an unvoiced sound, or background noise according to a recognition result obtained by the above method. The voiced/unvoiced sound analysis unit 120 may separate and output the voice frame as a voice sound, an unvoiced sound, or background noise according to a result of the determination.

The LPC processing unit 130 may find a formant energy by applying the LPC to a voice frame that is determined as a voiced sound by the voiced/unvoiced sound analysis unit 120. The LPC processing unit 130 may find a plurality of formant energies by applying the LPC to the voice frame according to different linear prediction orders. For example, the LPC processing unit 130 may find two formant energies by applying a 4th-order LPC and a 10th-order LPC to the voice frame. A method of performing signal processing by applying the LPC to voice signals was described in detail in Korean publication No. 10-2012-0074314 and Korean patent No. 10-0664271.

The alcohol consumption determination unit 140 may calculate differences among a plurality of formant energies that are generated by applying a plurality of linear predication orders. When the plurality of formant energies are found by applying a plurality of linear prediction orders to each voice frame received by the LPC processing unit 130, the alcohol consumption determination unit 140 finds differences among the plurality of formant energies for each voice frame.

The alcohol consumption determination unit 140 may find average energy of the differences among the formant energies of each voice frame. The alcohol consumption determination unit 140 may find a ratio of a previous video frame to a current voice frame among the received voice frames, count the number of voice frames having the ratio greater than a predetermined threshold, and find a ratio of the counted number to a total number of voice frames that are determined as voiced sounds to determine whether alcohol has been consumed.

This alcohol consumption determination method is possible because the formant energy is sensitive to an LPC order difference before drinking but not after drinking. After drinking, significant formant energy smoothing of the formant energy envelope of the voice frame occurs due to nasalization. Thus, a formant energy variation for an LPC order, in particular, a variation in the maximum of each formant energy tends to be shown as insensitive. Accordingly, the formant energy envelope is characterized to be insensitive to the LPC order difference compared to that before drinking.

FIG. 1B is a view showing an example in which a low pass filter (LPF) application unit 125 is added to a block of FIG. 1A.

The LPF application unit 125 may filter out only signals at a certain frequency or less by applying a low pass filter to voice signals separated as voiced sounds by the voiced/unvoiced sound analysis unit 120. The LPF application unit 125 is an optional element. The fourth formant energy F4 may be filtered out by passing only signals at 3.5 kHz or less.

That is, since the fourth formant energy in the voice signal is hardly changed by an articulator, the LPF application unit 125 may filter out harmonics including the fourth formant energy in order to reduce the amount of processing and may perform the processing only on filtered low-band signals.

Figure 2:
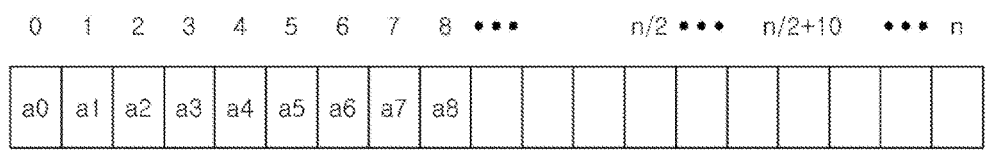
FIG. 2 is a view for describing a concept in which voice signals are converted into voice frames by a voice input unit included in the alcohol consumption determination terminal according to an embodiment of the present invention.

FIG. 2 is a view for describing a concept in which voice signals are converted into voice frames by a voice input unit included in the alcohol consumption determination terminal according to an embodiment of the present invention.

Typically, analog voice signals are sampled at a rate of 8000 per second and in the size of 16 bits (65535 steps) and converted into voice data.

The voice input unit 110 may convert received voice signals into voice data and convert the voice data into voice frame data in units of frames. Here, one piece of the voice frame data has 256 energy values.

As shown in FIG. 2, the voice data is composed of a plurality of voice frames (n=the number of frames, n=1, 2, 3, . . . ) according to an input voice.

The voice input unit 110 generates a voice frame and then sends information regarding the voice frame to the voiced/unvoiced sound analysis unit 120.

Figure 3:
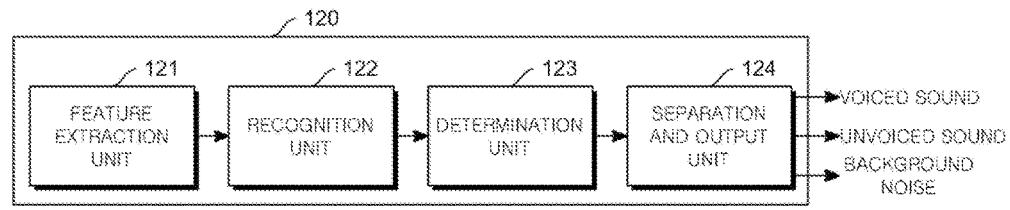
FIG. 3 is a control block diagram of a voiced/unvoiced sound analysis unit included in the alcohol consumption determination terminal according to an embodiment of the present invention.

FIG. 3 is a control block diagram of a voiced/unvoiced sound analysis unit included in the alcohol consumption determination terminal according to an embodiment of the present invention.

The voiced/unvoiced sound analysis unit 120 may include a feature extraction unit 121 configured to receive a voice frame and extract predetermined features from the voice frame, a recognition unit 122 configured to yield a recognition result for the voice frame, a determination unit 123 configured to determine whether the received voice frame is associated with a voiced sound or an unvoiced sound or whether the received voice frame is caused by background noise, and a separation and output unit 124 configured to separate and output the voice frame according to a result of the determination.

When the voice frame is received through the voice input unit 110, the feature extraction unit 121 may extract features such as periodic characteristics of harmonics or root mean square energy (RMSE) or zero-crossing count (ZC) of a low-band voice signal energy area from the received voice frame.

Generally, the recognition unit 122 may be composed of a neural network. This is because the neural network is useful in analyzing non-linear problems, that is, complicated problems that cannot be solved mathematically and thus is suitable for analyzing voice signals and determining whether a corresponding voice signal is a voiced signal, an unvoiced signal, or background noise according to a result of the analysis. The recognition unit 122, which is composed of such a neural network, may assign predetermined weights to the features extracted from the feature extraction unit 121 and may yield a recognition result for the voice frame through a calculation process of the neural network. Here, the recognition result refers to a value that is obtained by calculating calculation elements according to weights assigned to features of each voice frame.

The determination unit 123 may determine whether the received voice signal corresponds to a voiced sound or an unvoiced sound according to the above-described recognition result, that is, the value calculated by the recognition unit 122. The separation and output unit 124 may separate and output the voice frame as a voiced sound, an unvoiced sound, or background noise according to a result of the determination of the determination unit 123.

Meanwhile, since the voiced sound is distinctly different from the voiced sound and the background noise in terms of various features, it is relatively easy to identify the voiced sound, and there are several well-known techniques for this. For example, the voiced sound has periodic characteristics in which harmonics are repeated at a certain interval while the background noise does not have the harmonics. On the other hand, the unvoiced sound has harmonics with weak periodicity. In other words, the voiced sound is characterized in that the harmonics are repeated within one frame while the unvoiced sound is characterized in that the characteristics of the voiced sound such as the harmonics are repeated every certain number of frames, that is, is shown to be weak.

Figure 4A:
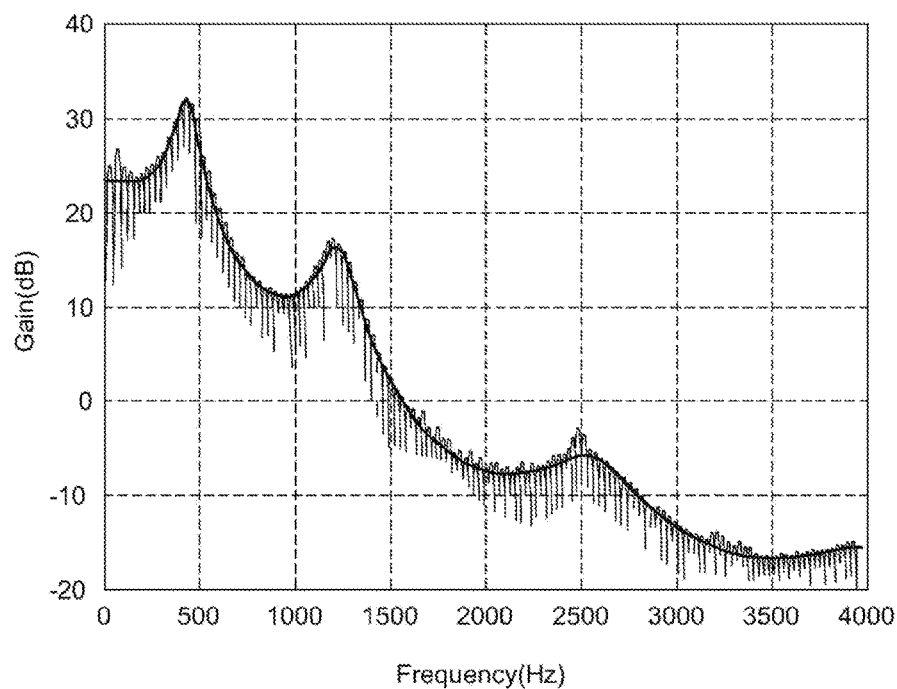
FIGS. 4A and 4B are graphs of formant energies of voice frames calculated by an LPC processing unit included in the alcohol consumption determination terminal according to an embodiment of the present invention.
Figure 4B:
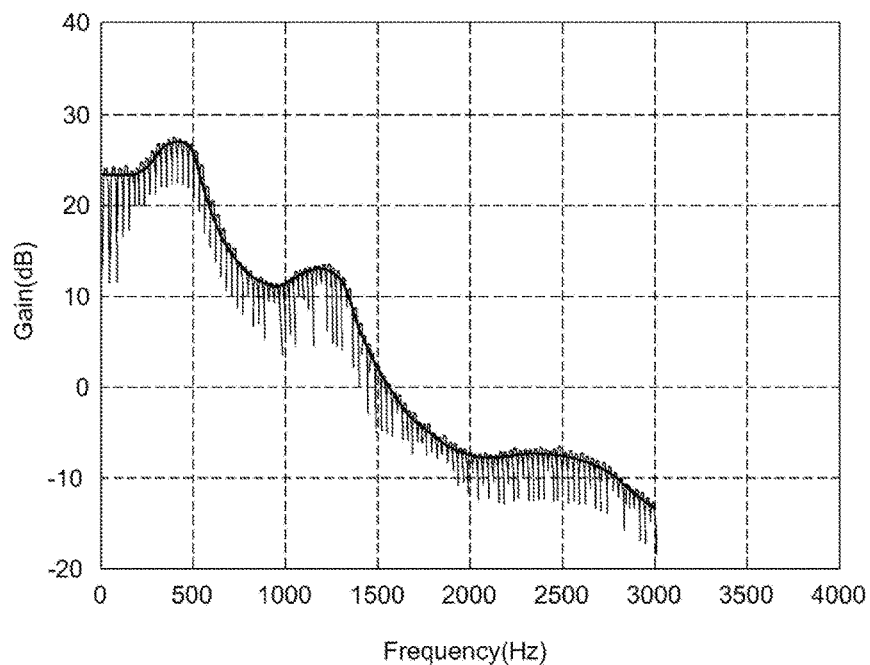

FIGS. 4A and 4B are graphs of formant energies of voice frames calculated by an LPC processing unit included in the alcohol consumption determination terminal according to an embodiment of the present invention.

As described above, the LPC processing unit 130 may find formant energies by applying a plurality of linear prediction orders to a voice frame that is determined as a voiced sound.

FIG. 4A shows a formant energy that is extracted by applying a high linear prediction order (e.g., 10th order), and FIG. 4B shows a formant energy that is extracted by applying a low linear prediction order (e.g., 4th order).

Linear prediction order information indicates the number of previous signals that are used to predict a current voice signal in linear predictive coding. Thus, it can be seen that the number of previous signals used for the prediction increases as the integer indicated by the linear prediction order information increases.

As described in FIGS. 4A and 4B, a graph of the formant energy extracted by applying a high linear prediction order is more accurate and sensitive because the current signal is predicted with reference to a larger number of previous signals, and a graph of the formant energy extracted by applying a low linear prediction order is relatively less sensitive because the current signal is predicted with reference to a smaller number of previous signals.

Figure 5:
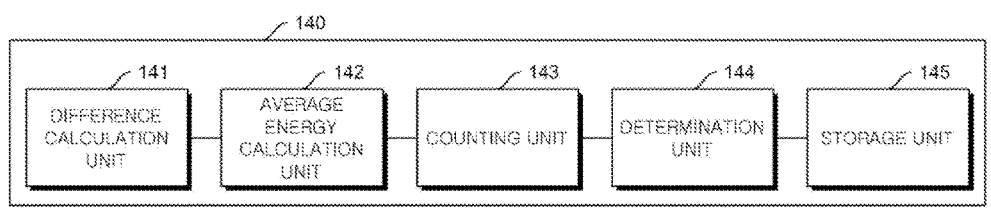
FIG. 5 is a control block diagram of an alcohol consumption determination unit included in the alcohol consumption determination terminal according to an embodiment of the present invention.
Figure 6:
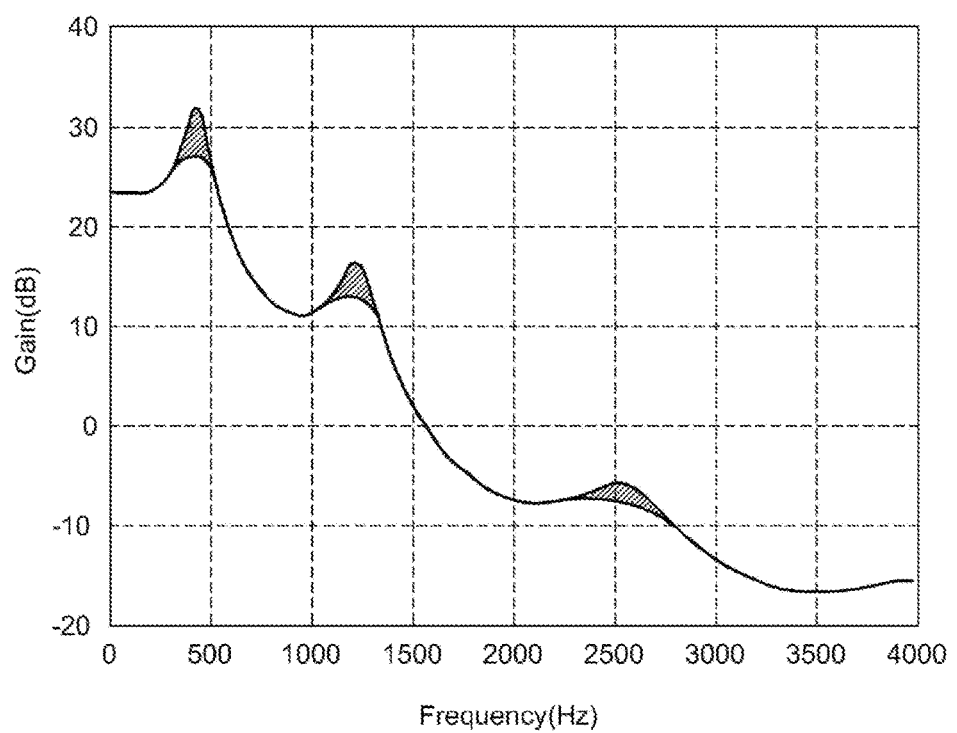
FIG. 6 is a graph showing differences among a plurality of formant energies that are calculated by a difference calculation unit of FIG. 5.

FIG. 5 is a control block diagram of an alcohol consumption determination unit included in the alcohol consumption determination terminal according to an embodiment of the present invention, and FIG. 6 is a graph showing differences among a plurality of formant energies that are calculated by a difference calculation unit of FIG. 5.

The alcohol consumption determination unit 140 may include a difference calculation unit 141, an average energy calculation unit 142, a counting unit 143, a determination unit 144, and a storage unit 145.

The difference calculation unit 141 may calculate differences among a plurality of formant energies that are generated by applying a plurality of linear perdition orders. Referring to FIG. 6, a difference between two formant energies is shown as the shaded region and may be represented by Equation 1 below:

$$FE\_distance(k) = FE\_L(k) - FE\_H(k) \qquad \text{[Equation 1]}$$

where FE_distance(k) is a function of changing the different between two formant energies into a distance (see the shaded region of FIG. 6), FE_L(k) is a formant energy that is extracted by applying a low linear prediction order (e.g., 4th order), and FE_H(k) is a formant energy that is extracted by applying a high linear prediction order (e.g., 10th order).

It will be appreciated that various linear prediction orders rather than the above-described 4th and 10th orders may be applied according to an embodiment of the present invention.

The average energy calculation unit 142 may calculate average energy of the differences among the plurality of formant energies that are calculated by the difference calculation unit 141. When the formant energies are extracted by applying the linear prediction orders to the voice frame determined as the voiced sound, and then the differences among the formant energies are calculated, the average energy calculation unit 142 may calculate average energy of the calculated differences among the formant energies for each voice frame with reference to Equation 2 below:

$$tEH(f) = \Sigma FE\_distance^2(k) \qquad \text{[Equation 2]}$$

where f is a frame number, and tEH(f) is average energy of differences among formant energies for each frame.

The counting unit 143 may find a ratio of average energy of differences among formant energies for each linear prediction order of the previous voice frame to average energy of differences among formant energies for each linear prediction order of the current voice frame. The counting unit 143 may find the ratio of the average energy of the formant energy differences of the previous frame to the average energy of the formant energy differences of the current frame by applying Equation 3 below:

$$tEH = \frac{tEH(f-1)}{tEH(f)} \qquad \text{[Equation 3]}$$

where tEH(f−1) is average energy of formant energy differences for each linear prediction order of the previous frame, tEH(f) is average energy of formant energy differences for each linear prediction order of the current frame, and tEH is a ratio of the average energy of the formant energy differences of the previous frame to the average energy of the formant energy differences of the current frame.

The counting unit 143 finds the ratio tEH of the average energy of the formant energy differences of the previous frame to that of the current frame for each voice frame determined as the voiced sound. The counting unit 143 increases a count value when the ratio that is found for each voice frame is greater than a predetermined threshold Vth; otherwise, the count value is maintained.

The determination unit 144 finds a ratio RATE of the counted number to the total number of voice frames determined as voiced sounds and determines if alcohol has been consumed when the ratio RATE is less than a predetermined value Rth. The determination unit 144 may calculate the ratio by Equation 4 below:

$$\text{Rate} = \frac{C}{T} \times 100 \qquad \text{[Equation 4]}$$

where Rate is a ratio of the counted number to the total number of voice frames, C is the counted number, and T is the total number of voice frames determined as voiced sounds.

The storage unit 145 may prestore the above-described threshold and ratio.

Figure 7:
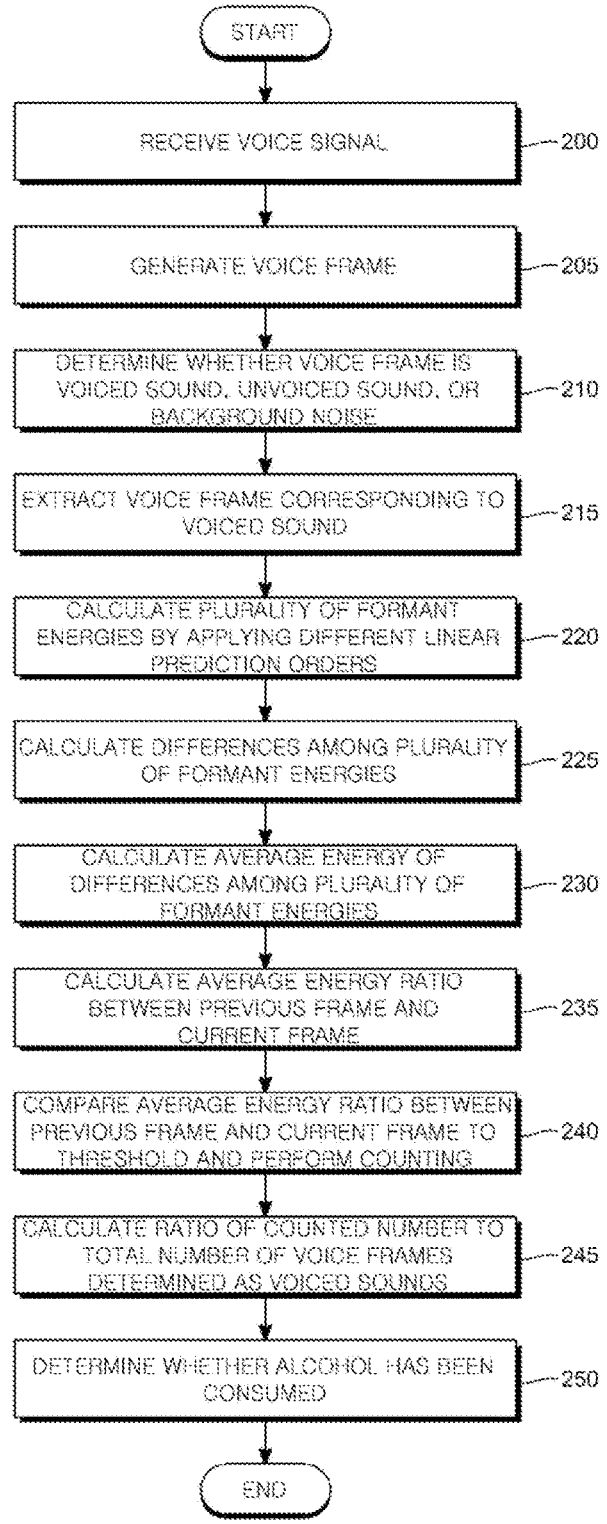
FIG. 7 is a control flowchart showing an alcohol consumption determination method according to an embodiment of the present invention.

FIG. 7 is a control flowchart showing an alcohol consumption determination method according to an embodiment of the present invention.

The voice input unit 110 may receive a person's voice, convert the received voice into voice data, convert the voice data into voice frames in units of frames, and output the voice frames (200 and 205).

The voiced/unvoiced sound analysis unit 120 may receive the voice frames, extract predetermined features, and analyze whether each of the received voice frames is associated with a voiced sound, an unvoiced sound, or background noise according to the extracted features (210).

The voiced/unvoiced sound analysis unit 120 may determine whether the voice frame corresponds to the voiced sound or the unvoiced sound according to a recognition result obtained by the above method and then may extract and output the voice frame corresponding to the voiced sound according to a result of the determination (215).

The LPC processing unit 130 may find a formant energy by applying linear predictive coding (LPC) to a voice frame that is determined as a voiced sound by the voiced/unvoiced sound analysis unit 120. The LPC processing unit 130 may find a plurality of formant energies by applying the LPC to the voice frame according to different linear prediction orders (220).

The alcohol consumption determination unit 140 may calculate differences among a plurality of formant energies that are generated by applying a plurality of linear predication orders. When the plurality of formant energies are found by applying a plurality of linear prediction orders to each voice frame received by the LPC processing unit 130, the alcohol consumption determination unit 140 finds differences among the plurality of formants for each voice frame (225).

The alcohol consumption determination unit 140 may find average energy of the differences among the formant energies of each voice frame (230).

The alcohol consumption determination unit 140 finds an average energy ratio between a previous voice frame and a current voice frame and counts the number of voice frames each having an average energy ratio greater than a predetermined threshold (235 and 240).

The alcohol consumption determination unit 140 calculates a ratio of the number of voice frames counted in step 240 to the total number of voice frames determined as voiced sounds and determines that alcohol has been consumed when the ratio is less than a predetermined value Rth; otherwise, it is determined that alcohol has not been consumed (245 and 250).

A recording medium having a computer program recorded thereon for executing the above-described alcohol consumption determination method is included in an embodiment of the present invention and is readable by a computer.

Figure 8:
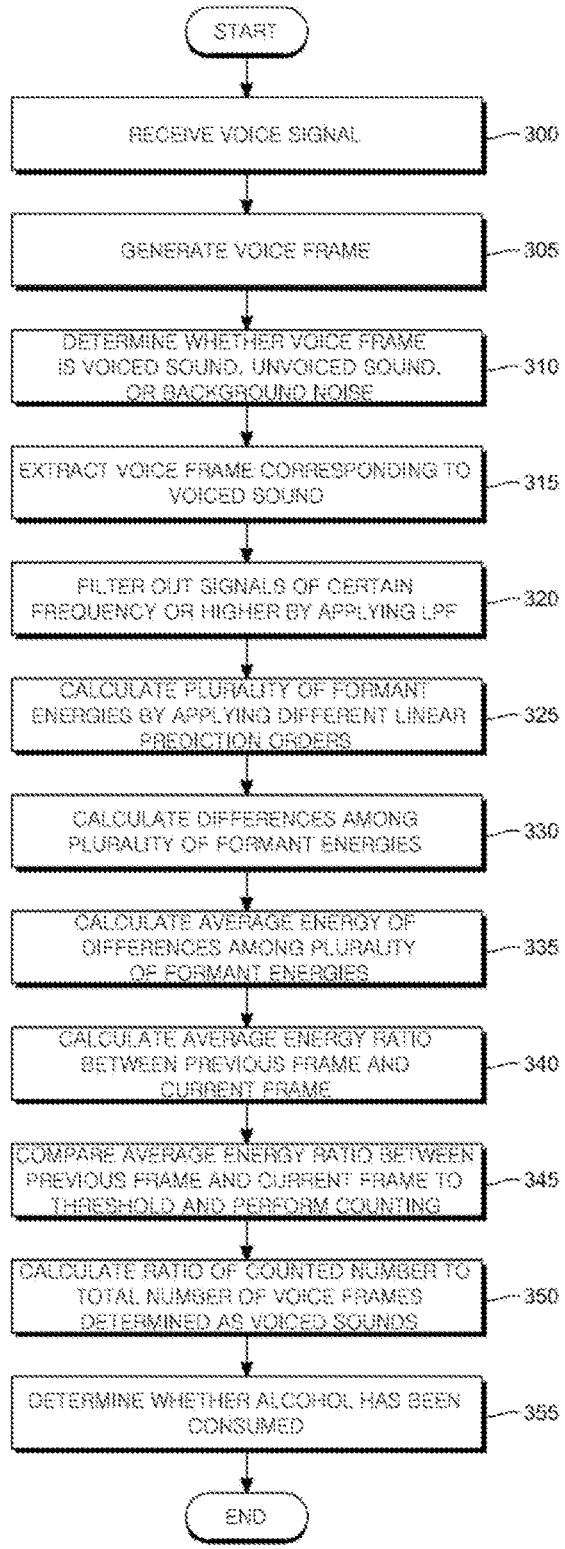
FIG. 8 is a control flowchart showing an alcohol consumption determination method according to another embodiment of the present invention.

FIG. 8 is a control flowchart showing an alcohol consumption determination method according to another embodiment of the present invention.

Compared to the control method of FIG. 7, step 320 is added to the control method of FIG. 8. Since the other steps are the same as those of FIG. 7, descriptions thereof will be omitted.

In step 320, when the voice frame corresponding to the voiced sound is extracted by the voiced/unvoiced sound analysis unit 120, the LPF application unit 125 filters out harmonics of a certain frequency or higher (e.g., 3.5 kHz) by applying a low pass filter. For example, the amount of processing may be reduced by filtering out voice signals with frequencies corresponding to a fourth formant or higher among frequencies corresponding to a first formant, a second formant, a third formant, a fourth formant, and a fifth formant.

Although the present invention has been described with reference to exemplary embodiments thereof, it should be understood that numerous other modifications and variations can be made without departing from the spirit and scope of the present invention by those skilled in the art. It is obvious that the modifications and variations fall within the spirit and scope thereof.

The invention claimed is:

1. A method for determining whether alcohol is consumed by a person in a vehicle, the method comprising:
receiving a voice signal from the said person in the vehicle and converting the received voice signal into a plurality of voice frames;
extracting a voice frame corresponding to a voiced sound from among the plurality of voice frames;
calculating a plurality of formant energies by applying linear predictive coding according to a plurality of linear prediction orders to the extracted voice frame;
computing differences among the plurality of formant energies;
determining whether alcohol is consumed by said person in the vehicle according to the computed differences; and
enabling or disabling the vehicle based on the determination.

2. The method of claim 1, wherein the extracting a voice frame corresponding to a voiced sound among the plurality of voice frames comprises:
extracting predetermined features from a voice frame among the plurality of voice frames, and
determining whether said voice frame is from a voiced sound, an unvoiced sound, or background noise.

3. The method of claim 2, wherein the predetermined features comprise periodic characteristics of harmonics, root mean square energy (RMSE), or zero-crossing count (ZC) of a low-band voice signal energy area.

4. The method of claim 2, wherein the determining whether said voice frame is from a voiced sound, an unvoiced sound, or background noise comprises using neural network.

5. The method of claim 1, wherein the calculating a plurality of formant energies by applying linear predictive coding according to a plurality of linear prediction orders to the extracted voice frame comprises applying a low order linear prediction order and a high order linear prediction order to the extracted voice frame thereby calculating formant energies according to the applied linear prediction orders.

6. The method of claim 5, wherein the computing differences among the plurality of formant energies comprises calculating a difference between the formant energy according to the applied low order linear prediction order and the formant energy according to the applied high order linear prediction order.

7. The method of claim 1, wherein the determining whether alcohol is consumed by said person according to the computed differences comprises:
calculating an average energy of the differences among the plurality of formant energies for the voice frame,
calculating a ratio of average energies between a previous voice frame and a current voice frame for each of the voice frames
counting the number of voice frames each having the ratio of average energies greater than a predetermined threshold, and
determining whether alcohol is consumed by said person according to the counted number.

8. The method of claim 7, wherein the determining whether alcohol is consumed by said person according to the counted number comprises:
calculating a ratio between the counted number and the total number of voice frames determined as the voiced sounds,
determining that alcohol is consumed by said person when the calculated ratio is less than a predetermined value, and
determining that alcohol is not consumed by said person when the calculated ratio is greater than the predetermined value.

9. The method of claim 1, further comprising filtering out harmonics of a certain frequency or higher by applying a low pass filter to the extracted voice frame.

10. A non-transitory computer-readable recording medium having a program recorded thereon for performing a method for determining whether alcohol is consumed by a person in a vehicle, the method comprising:
receiving a voice signal from the said person in the vehicle and converting the received voice signal into a plurality of voice frames;
extracting a voice frame corresponding to a voiced sound from among the plurality of voice frames;
calculating a plurality of formant energies by applying linear predictive coding according to a plurality of linear prediction orders to the extracted voice frame;
computing differences among the plurality of formant energies;
determining whether alcohol is consumed by said person in the vehicle according to the computed differences; and
enabling or disabling the vehicle based on the determination.

11. The non-transitory computer-readable recording medium of claim 10, wherein the extracting a voice frame corresponding to a voiced sound among the plurality of voice frames comprises:
extracting predetermined features from a voice frame among the plurality of voice frames, and
determining whether said voice frame is from a voiced sound, an unvoiced sound, or background noise.

12. The non-transitory computer-readable recording medium of claim 11, wherein the predetermined features comprise periodic characteristics of harmonics, root mean square energy (RMSE), or zero-crossing count (ZC) of a low-band voice signal energy area.

13. The non-transitory computer-readable recording medium of claim 11, wherein the determining whether said voice frame is from a voiced sound, an unvoiced sound, or background noise comprises using neural network.

14. The non-transitory computer-readable recording medium of claim 10, wherein the calculating a plurality of formant energies by applying linear predictive coding according to a plurality of linear prediction orders to the extracted voice frame comprises applying a low order linear prediction order and a high order linear prediction order to the extracted voice frame thereby calculating formant energies according to the applied linear prediction orders.

15. The non-transitory computer-readable recording medium of claim 14, wherein the computing differences among the plurality of formant energies comprises calculating a difference between the formant energy according to the applied low order linear prediction order and the formant energy according to the applied high order linear prediction order.

16. The non-transitory computer-readable recording medium of claim 10, wherein the determining whether alcohol is consumed by said person according to the computed differences comprises:

calculating an average energy of the differences among the plurality of formant energies for the voice frame, calculating a ratio of average energies between a previous voice frame and a current voice frame for each of the voice frames counting the number of voice frames each having the ratio of average energies greater than a predetermined threshold, and determining whether alcohol is consumed by said person according to the counted number.

17. The non-transitory computer-readable recording medium of claim 16, wherein the determining whether alcohol is consumed by said person according to the counted number comprises: calculating a ratio between the counted number and the total number of voice frames determined as the voiced sounds, determining that alcohol is consumed by said person when the calculated ratio is less than a predetermined value, and determining that alcohol is not consumed by said person when the calculated ratio is greater than the predetermined value.

18. The non-transitory computer-readable recording medium of claim 10, further comprising filtering out harmonics of a certain frequency or higher by applying a low pass filter to the extracted voice frame.

* * * * *